United States Patent [19]

Viazis

[11] Patent Number: 5,302,116
[45] Date of Patent: Apr. 12, 1994

[54] ORTHODONTIC BRACKET

[76] Inventor: Anthony D. Viazis, 373 E. Las Colinas Blvd., Apt. 368, Irving, Tex. 75039

[21] Appl. No.: 45,277

[22] Filed: Apr. 7, 1993

Related U.S. Application Data

[63] Continuation of Ser. No. 854,571, Mar. 20, 1992, abandoned.

[51] Int. Cl.$^5$ .............................................. A61C 3/00
[52] U.S. Cl. ........................................ 433/8; 433/10
[58] Field of Search ............... 433/8, 9, 10, 11, 12, 433/13, 14, 15, 16, 17

[56] References Cited

U.S. PATENT DOCUMENTS

| | | | |
|---|---|---|---|
| 1,991,047 | 2/1935 | Boyd et al. | 32/14 |
| 2,236,042 | 3/1941 | Terwilliger | 32/14 |
| 2,527,526 | 10/1950 | Brusse | 32/14 |
| 2,854,747 | 10/1958 | Lewis | 32/14 |
| 2,958,945 | 11/1960 | Waldman | 32/14 |
| 2,971,258 | 2/1961 | Bien | 32/14 |
| 3,110,105 | 11/1963 | Berman et al. | 32/14 |
| 3,164,901 | 1/1965 | Wallshein | 32/14 |
| 3,292,260 | 12/1966 | Jenkins | 32/14 |
| 3,374,542 | 3/1968 | Moylan | 32/14 |
| 3,414,976 | 12/1968 | Steiner | 32/14 |
| 3,461,558 | 8/1969 | Miller et al. | 32/14 |
| 3,477,128 | 11/1969 | Andrews | 32/14 |
| 3,504,438 | 4/1990 | Wittman et al. | 32/14 |
| 3,626,593 | 12/1971 | Ridgeway | 32/14 A |
| 3,765,091 | 10/1973 | Northcutt | 32/14 A |
| 3,922,787 | 12/1975 | Fischer et al. | 433/8 X |
| 4,227,876 | 10/1980 | Fogel et al. | 433/11 |
| 4,386,908 | 6/1983 | Kurz | 433/8 X |
| 4,416,627 | 11/1983 | Beazley | 433/18 |
| 4,531,911 | 7/1985 | Creekmore | 433/8 |
| 4,536,154 | 9/1985 | Garton, Jr. et al. | 433/8 |
| 4,551,094 | 11/1985 | Kesling | 433/8 |
| 4,565,526 | 1/1986 | Kawata et al. | 433/8 |
| 4,575,337 | 3/1986 | Fujita | 433/8 |
| 4,582,487 | 4/1986 | Creekmore | 433/8 |
| 4,659,309 | 4/1987 | Merkel | 433/9 |
| 4,664,626 | 5/1987 | Kesling | 433/8 X |
| 4,712,999 | 12/1987 | Rosenberg | 433/8 |
| 4,799,882 | 1/1989 | Keslingg | 433/8 |
| 4,838,786 | 6/1989 | Reher et al. | 433/9 |
| 4,838,787 | 6/1989 | Lerner | 433/14 |
| 4,842,512 | 6/1989 | Kesling | 433/8 |
| 4,877,398 | 10/1989 | Kesling | 433/8 |
| 4,917,602 | 4/1990 | Broussard | 433/8 |
| 4,927,360 | 5/1990 | Pospisil | 433/8 |
| 4,941,825 | 7/1990 | Lerner | 433/14 |
| 5,037,297 | 8/1991 | Lerner | 433/14 |

OTHER PUBLICATIONS

Unitek Corporation flyer illustrating the "Unitwin" bracket.
Unitek Product Catalog illustrating the "Glance" bracket.
ORMCO Product Catalog 1983 (pp. V-11, 20, 21, 23).
Unitek Product Catalog 1978 (pp. 31-33).
Mechanical Principles in Orthodontic Force Control (pp. 246-269, 296-311).

Primary Examiner—John G. Weiss
Assistant Examiner—Nicholas D. Lucchesi
Attorney, Agent, or Firm—Kenyon & Kenyon

[57] ABSTRACT

An orthodontic bracket is provided for use with an arch wire to apply corrective forces to a tooth. The bracket includes a vertical member having a slot formed therein for receiving the arch wire and a wide base horizontal member connected to the vertical member. The vertical member is positioned gingivally with respect to the horizontal member. The horizontal member includes opposing first and second ends that extend away from the vertical member and define a pair of spaced-apart wire engaging points engageable with the arch wire during treatment.

15 Claims, 3 Drawing Sheets

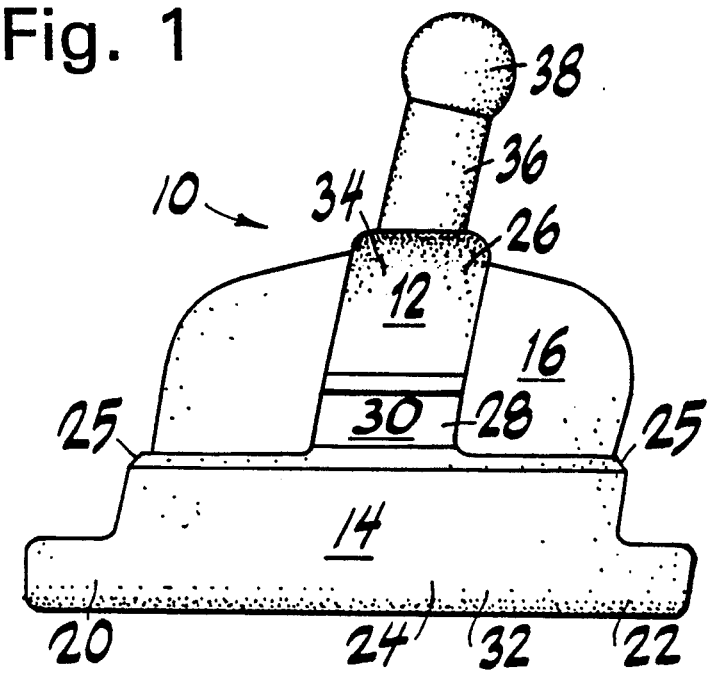
Fig. 1
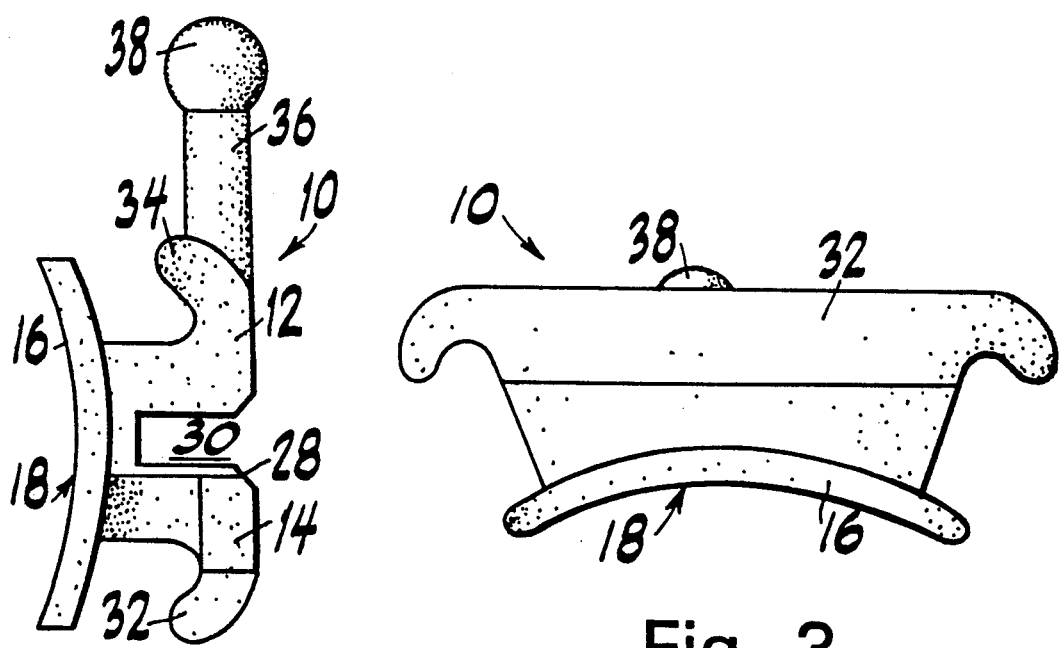
Fig. 2
Fig. 3

Fig. 4a
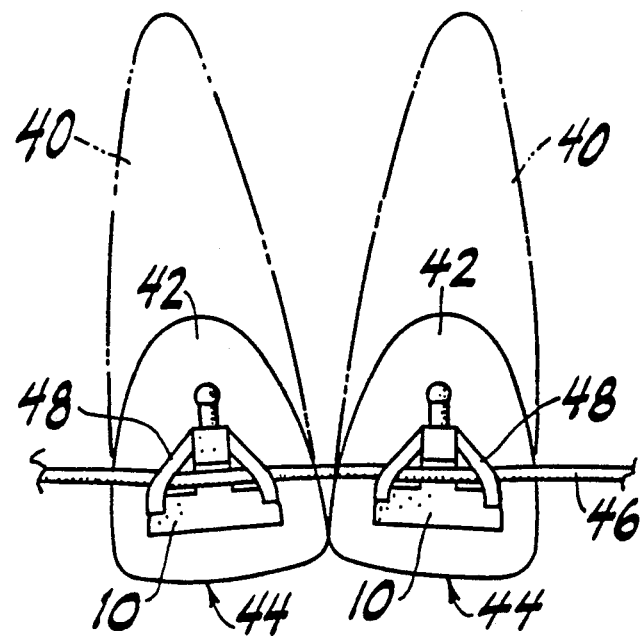
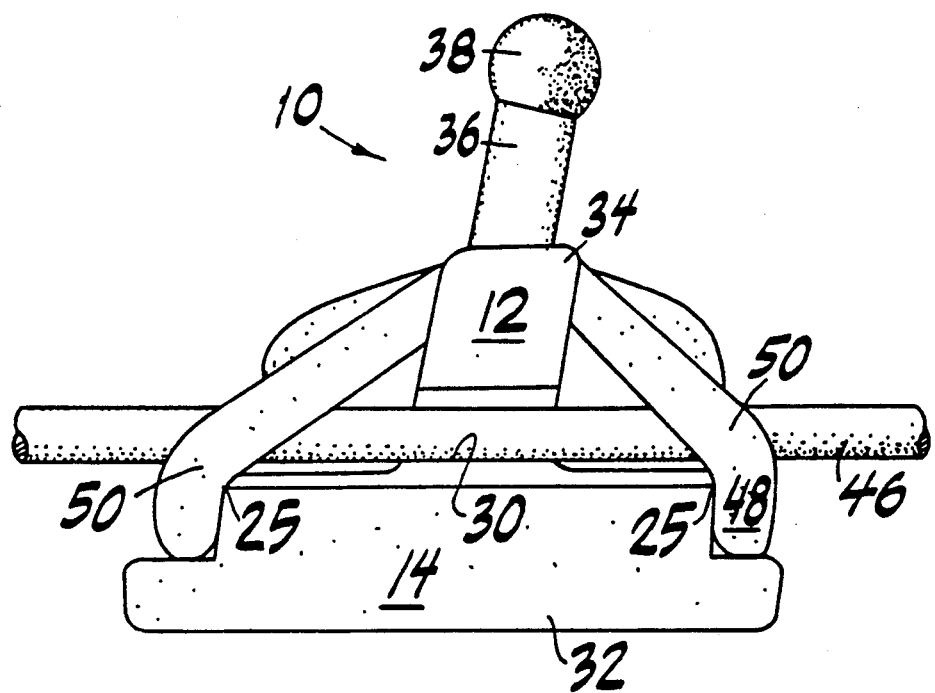
Fig. 5

ORTHODONTIC BRACKET

This application is a continuation of application Ser. No. 07/854,571, filed on Mar. 20, 1992, and now abandoned.

FIELD OF THE INVENTION

This invention relates generally to orthodontic appliances and, more particularly, to orthodontic brackets used in corrective orthodontic treatment.

BACKGROUND INFORMATION

Orthodontic appliances are used for applying corrective forces to misaligned teeth. The appliances generally include brackets, which are mounted on the teeth, arch wires slidingly mounted in the brackets for applying forces and for guiding movement, and elastics or other force transmitting members connected to the brackets for applying additional corrective forces to the teeth.

Conventional brackets generally include a base portion, which abuts the tooth surface, an outer portion, which has a slot formed therein for receiving an arch wire, and hook members, on which elastics, ligatures or other force transmitting members can be attached.

A typical single bracket has an outer portion comprising a single vertically-oriented bar with a small horizontal slot formed therein for receiving the arch wire. Twin brackets have an outer portion comprising a pair of parallel, vertically-oriented bars that are spaced apart with a slot cut in each bar to receive the arch wire. Other brackets of various shapes are known including a bracket having an outer portion with a generally "Y" shape with an arch wire slot formed therein.

Single wing brackets that are narrow in width or have small slots create smaller moments from the contact between the arch wire and the bracket, thereby making torque, tip and rotational control difficult during tooth movement. Also, such brackets frequently cause entrapment of food and are hygienically not the most desirable.

Many known brackets including typically twin type brackets have large widths or long arch wire slots to increase the magnitude of moments created by contact between the arch wire and the slot. By increasing the moments, tip, torque and rotational control of the teeth is enhanced during tooth movement. However, one disadvantage to having such long slots or large bracket widths is that it reduces the inter-bracket distance or the distance between brackets on adjacent teeth. Consequently, the span of the arch wire between the brackets is small, which reduces the flexibility of the wire and makes it difficult to control forces exerted by the wire.

Another problem with brackets having long arch wire slots is that there may be substantial undesirable friction between the arch wire and the bracket during tooth movement. Additionally, brackets having large widths are difficult to place and orient on the tooth.

Accordingly, one object of this invention is to provide a bracket that has excellent rotational, tip and torque control, yet provides sufficiently large inter-bracket distances to enable effective use of arch wires and to reduce friction between the bracket and the arch wire. Another object of this invention to provide a bracket that is easy to orient and position on the tooth surface.

SUMMARY OF THE INVENTION

The present invention is directed to an orthodontic bracket for use with an arch wire for applying corrective forces to a tooth. The orthodontic bracket includes a vertical member connected to a horizontal member. The vertical member is positioned gingivally with respect to the horizontal member and includes a slot therein for receiving the arch wire. The horizontal member includes opposing first and second ends that extend away from the vertical member and define a pair of spaced-apart wire engaging points engageable with the arch wire as the tooth rotates during treatment.

Brackets constructed in accordance with the present invention have small arch wire slots and large inter-bracket distances. Consequently, the arch wire span between brackets is large, enhancing the flexibility of the arch wire and enabling greater control over the forces exerted by the arch wire. The small slot size also reduces friction between the arch wire and the slot during tooth movement. Furthermore, the brackets provide excellent rotational, torque and tip control because of their general delta shape with spaced apart wire engaging points.

Brackets in accordance with the invention are particularly suited for the tooth to which they are applied. In this regard, applicant's customized delta shaped bracket is provided with a horizontal member of a width of between 60–90% of the width of the tooth, preferably between 65–85%. The wide based delta shaped bracket provides an increased moment to improve tooth control with a large inter-bracket slot distance to improve arch wire performance.

The bracket is provided with rounded corners and edges to reduce irritation and increase wearing comfort.

BRIEF DESCRIPTION OF THE DRAWINGS

The foregoing and additional objects and advantages of the invention will become more apparent in view of the following detailed description and drawings, in which like reference characters denote like parts.

FIG. 1 is a front view of a bracket constructed in accordance with the present invention.

FIG. 2 is a side view of the bracket shown in FIG. 1.

FIG. 3 is a bottom view of the bracket shown in FIGS. 1 and 2.

FIG. 4a illustrates the placement of two brackets on teeth.

FIG. 5 is an enlarged view of one of the brackets shown in FIG. 4a.

DETAILED DESCRIPTION

Figure 4B:
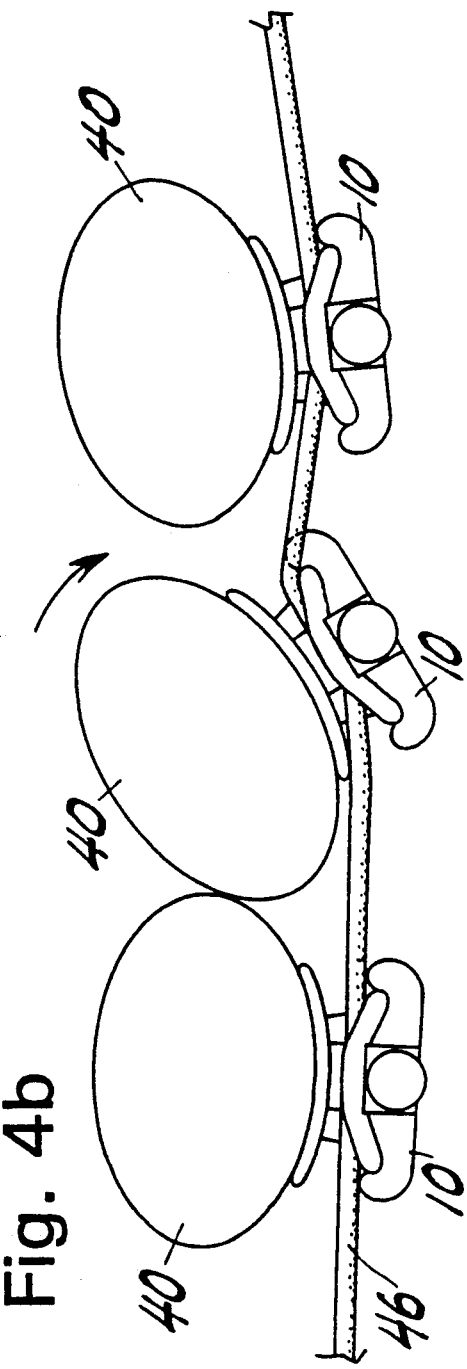
FIG. 4b is a plan view illustrating corrective rotational movement of a tooth.

FIGS. 1–3 illustrate the front, side and bottom views, respectively of an orthodontic bracket generally indicated by reference character 10 in accordance with the present invention. The bracket 10 includes a vertical extending bar-like member or element 12, a horizontal extending bar-like member or element 14 and an underlying base portion 16.

As shown in FIGS. 2 and 3, the base portion 16 includes a tooth abutting surface 18, which is generally contoured to fit the outer shape of a tooth (not shown). The surface 18 is designed to receive adhesive material for bonding the bracket 10 to the tooth.

The horizontal bar 14 includes a first end 20 and an opposing second end 22 with a middle portion 24 therebetween. The ends 20 and 22 of the horizontal bar 14 extend horizontally and away from the middle portion 24, thereby forming two spaced apart wire engaging points 25 at upper corners of the horizontal bar 14.

The vertical bar 12 includes a first end portion 26 and an opposing second end portion 28. The second end portion 28 is connected to the horizontal bar 14 proximate the middle portion 24. The vertical and horizontal bars 12 and 14 may be joined together or formed integrally. When positioned on either upper or lower teeth, the vertical bar 12 will extend gingivally with respect to the horizontal bar 14 and generally in line with the axis of the tooth. (See FIG. 4a).

The vertical bar 12 has a height approximately equal to the width of the horizontal bar 14. The bars 12 and 14 may be perpendicular to each other. Alternately, as shown in FIG. 1, the angle between the bars 12 and 14 may be varied from 90° to accommodate the shape of particular teeth as will be discussed later. Preferably, the width of vertical bar 12 is approximately equal to that of a typical single wing bracket. Also, the length of the horizontal bar 14 is preferably customized for the tooth to which it is applied and is generally equal to or greater than the width of a typical twin bracket. More specifically, it has been found that for smaller teeth such as a lower center incisor, the horizontal bar is 3.2 mm. Similarly, for a cuspid or larger tooth, the horizontal bar is 6 mm. In this regard, it has been found that the horizontal bar should cover between 60-90% of the width of the tooth to which is it to be applied, the most preferred range being 65-85%.

An arch wire slot 30 is formed in the vertical bar 12 at the second end portion 28. The arch wire slot 30 is designed to receive an orthodontic arch wire (not shown) as will be further discussed with reference to FIGS. 4a and 5. As FIG. 2 indicates, the entrance to the slot 30 is chamfered at 28 to allow easy insertion of the arch wire. The slot 30 can be formed parallel to the horizontal bar 14 or at any angle thereto for enabling the arch wire to exert torque on the tooth. The slot 30 is slightly elevated from the horizontal bar 14 to avoid friction (See FIG. 5).

The horizontal bar 14 includes an edgewise tie-wing 32 projecting downwardly along the length of the horizontal bar 14. Similarly, the vertical bar 12 includes an upwardly projecting tie-wing 34 at the first end portion 26. The tie-wings 32 and 34 are designed to receive an o-ring, elastic chain, ligature wire or other securing device (not shown) as will be further discussed with reference to FIGS. 4a and 5.

An optional ball hook member 36 extends gingivally from the first end portion 26 of the vertical bar 12. The ball hook member 36 includes an enlarged ball portion 38 for facilitating the attachment of ligatures, elastics, coil springs or other force transmitting members (not shown). Although not shown, the ball hook member 36 may be replaced with a power arm or with other hook devices.

The bracket 10 may be formed of stainless steel material. Stainless steel, however, is only exemplary and can be changed as desired to ceramic, plastic or other suitable material.

As FIGS. 1-3 show, the edges and corners of the bracket 10 are generally rounded to reduce irritation and increase wearing comfort to the patient.

FIG. 4a illustrates the placement of two brackets 10 on two upper teeth 40. FIG. 5 is an enlarged view of one of the brackets 10 shown in FIG. 4a. The teeth 40 include exposed crown portions 42 with occlusal surfaces 44 at the ends thereof. Each bracket 10 is generally centrally positioned on a crown portion 42 such that the vertical bar 12 and hook portion 36 are generally aligned with the long axis of the tooth 40 and the horizontal bar 14 is generally parallel to the occlusal surface 44. The bracket slot 30 is preferably positioned on the "F.A." point of the tooth, which is the midpoint of the crown 42 along the long axis.

When the bracket 10 is mounted on either a patient's upper or lower teeth, it is oriented such that the horizontal bar 14 is near the occlusal surface of the tooth and the vertical bar 12 extends gingivally from the horizontal bar 14.

The vertical and horizontal bars 12 and 14 may be perpendicular to each other. However, the angle between the bars 12 and 14 may be varied from 90° to accommodate teeth having occlusal surfaces that are not perpendicular to the tooth's long axis. In this case, use of a modified bracket is preferred so that the vertical bar 12 is aligned with the tooth's long axis and the horizontal bar 14 is parallel to the tooth's occlusal surface.

Because the bracket 10 can be oriented on a tooth by aligning the vertical bar 12 with the long axis of the tooth, placement of the bracket 10 on a tooth is easy compared to many conventional brackets. Consequently, fewer brackets will be placed improperly, reducing the need for arch wire bending to compensate for improper bracket placement. With fewer bends in the arch wire, the wire can slide through the brackets more easily, enabling more effective space closure.

As shown in FIGS. 4a and 5, an arch wire 46 is positioned in the slots 30 in each of the brackets 10. Also, an elastic o-ring 48 is coupled with each of the brackets 10 to hold the arch wire 46 in place. Although not shown, the o-ring 48 may be replaced by a ligature wire or other fastening member or an elastic chain or other force transmitting member.

Figure 4C:
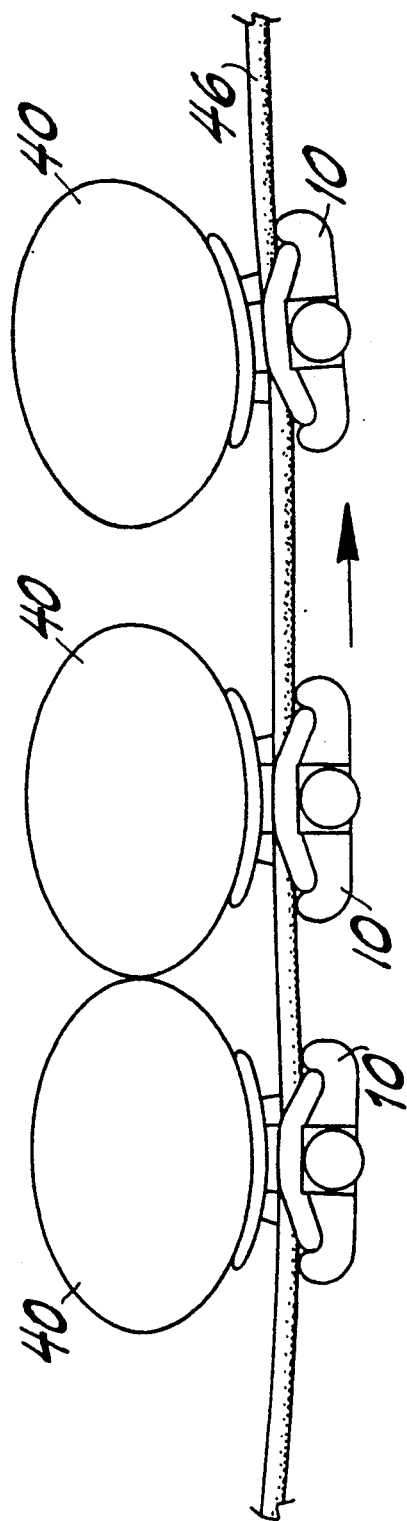
FIG. 4c is a plan view illustrating corrective sideward movement of a tooth.

FIGS. 4a, 4b and 4c illustrate some of the advantages of the bracket 10. First, because the vertical bar 12 is narrow and the slot 30 is small relative to the rest of the bracket 10 and the crown 42, the inter-bracket distance between the slots 30 of adjacent brackets 10 is large. A large inter-bracket distance is advantageous as it increases the span of the arch wire 46, thereby enhancing its flexibility and allowing greater control of the forces exerted by the arch wire. With larger inter-bracket distances a practitioner can advantageously use Neosentalloy for the arch wire in both the initial and finishing stages of treatment. With conventional brackets, Neosentalloy wire can usually be used during the initial stages of treatment and followed with use of a stainless steel wire.

The reduced width of the slots 10 is also advantageous as it reduces friction between the wire 46 and the bracket 10 during tooth movement. In particular, with bracket slots on posterior teeth, resistance to wire movement resulting from rotational forces at the mesiobuccal and distolingual areas of the slots is reduced. Similarly, resistance from tipping forces at the mesio-occlusal and distogingival areas of posterior bracket slots is reduced. Any torsional resistance at other contact areas of the slots is also reduced.

As shown in FIG. 5, after the arch wire 46 is positioned in the slot 30, the o-ring 48 is secured to the bracket 10 beneath the tie-wings 32 and 34 and over the arch wire 46 to form a general delta shaped configuration. The arch wire 46 is thereby secured to the bracket 10.

FIG. 5 illustrates additional advantages of the bracket 10. First, because of the configuration of the bracket 10, the o-ring 48 forms a generally triangular or delta shape when in place over the arch wire 46. The o-ring 48 contacts the arch wire 46 near the base of this triangular shape at contact points 50, which are relatively widely spaced apart and generally located over contact points 25.

Contact points 25 identify where the arch wire 46 contacts bracket 10 during corrective rotational force applied to a misaligned tooth. The ratio of the distance between the wire engaging ponts 25 to the length of the slot 30 is approximately 3.5:1. The large spacing between contact points 25 allowed by the wide delta shaped bracket enables the bracket 10 to develop sufficiently large moments for proper rotational control of the tooth. Because forces applied to a tooth during tooth movement are applied at the surface of the tooth through the bracket 10 rather than at the tooth's center of resistance, the tooth develops a tendency to rotate. The contact of the arch wire 46 at contact points 25 and held by the o-ring 48 provides sufficiently large corrective moments to enhance tooth rotation control because of the large rotational moment as seen in FIG. 4b. In addition, it should be noted that the bracket 10 can be used with an arch wire to apply corrective forces to straighten teeth that are initially spaced as shown in FIG. 4c. Then it is noted that the shortened distance between brackets provided by the wide horizontal bar of bracket 10 tends to prevent undesired rotation and provide movement along the direction of the arch wire.

When the arch wire 46 is initially positioned in the slot 30, it may be parallel to and slightly above the horizontal bar 14 as shown in FIG. 5. During use, tipping of the tooth may occur as the forces applied to the tooth are applied on the crown of the tooth and not on the tooth's center of resistance. The bracket 10, however, inhibits tipping by the contact between the arch wire 46 and one of the wire engaging points 25, which creates sufficiently large moments to deter the tipping. On posterior teeth, tip control reduces mesial tipping of the teeth in extraction sites and thereby reduces the risk of lateral open bites during closure.

Although the present invention has been described with respect to specific embodiments, various changes and modifications may be suggested to one skilled in the art, and it is intended that the present invention encompasses such changes and modifications as fall within the scope of the appended claims.

I claim:

1. An orthodontic bracket for use with an arch wire to apply corrective forces to a tooth, comprising:
   a substantially vertical element having a slot formed therein for receiving the arch wire; and
   a substantially horizontal element connected to said vertical element with said vertical element being positioned gingivally with respect to said horizontal element, said horizontal element having opposing first and second ends extending away from said vertical element and defining a pair of spaced-apart wire engaging points engageable with the arch wire for enabling proper rotational control of the bracket during use, said slot in said vertical element having its lower surface vertically spaced from said horizontal element to limit contact between the arch wire and said horizontal element, said horizontal member having at the ends thereof horizontally extending wings for engaging stretched elastomeric modules thereby enhancing rotational control.

2. The orthodontic bracket of claim 1, further comprising a first tie-wing on said vertical element and a second tie-wing on said horizontal element to enable attachment of a fastening member to the bracket for securing the arch wire in said slot.

3. The orthodontic bracket of claim 2, wherein said horizontal element is customized to the tooth to which it is applied and of a length at least equal to between 60–90% of the width of the tooth to which it is applied to provide a substantial distance between said engaging points on said second tie-wing.

4. The orthodontic bracket of claim 2, wherein the width of said vertical element is approximately equal to that of a standard single wing bracket and the width of said horizontal element is between 65–85% of the width of the tooth to which it is applied.

5. The orthodontic bracket of claim 2, wherein the fastening member forms a generally delta shape when attached to the bracket, the generally delta shape having a base near said horizontal element, and wherein the arch wire contacts the fastening member near the base at spaced-apart contact points.

6. The orthodontic bracket of claim 2, wherein said horizontal element has a length between 3.2 and 6 mm.

7. The orthodontic bracket of claim 1 wherein said vertical element and said horizontal element are connected such that said vertical element is adapted to be aligned with the long axis of the tooth and said horizontal element is parallel to the occlusal surface of the tooth.

8. The orthodontic bracket of claim 1, wherein said vertical and horizontal elements have rounded edges and corners to reduce irritation and to increase wearing comfort.

9. The orthodontic bracket of claim 1, further comprising a hook member connected to said vertical element for attaching a force transmitting member to the bracket, said hook member including an enlarged ball portion.

10. The orthodontic bracket of claim 1, further comprising a first tie-wing on said vertical element, a second tie-wing on said horizontal element, and a fastening member attached to said tie-wings for securing the arch wire in said slot.

11. The orthodontic bracket of claim 10, wherein the arch wire used with the bracket is adapted to engage said spaced apart wire engaging points during treatment and said fastening member is attached to the bracket such that said fastening member contacts the arch wire at a pair of spaced-apart contact points to ensure and maintain the arch wire in engagement with at least one of said engaging points to provide rotational control to the bracket.

12. An orthodontic bracket for attachment to a tooth comprising:
   a vertical member having opposing first and second end portions, said vertical member having a slot formed therein for receiving an arch wire; and
   a horizontal member having opposing first and second ends with a middle portion therebetween, said vertical member being of a length approximately equal to the width of said horizontal member and being joined to said horizontal member proximate said middle portion with said vertical member being positioned gingivally with respect to said horizontal member, said first and second ends of said horizontal member projecting horizontally away from said middle portion and defining a pair of spaced-apart wire engaging points engageable with the arch wire to provide rotational control of the bracket, said slot in said vertical member being vertically spaced apart from said middle portion of said horizontal member so that the arch wire is not in contact with said middle portion, and wherein the ratio of the distance between the wire engaging points to the length of the slot is approximately 3.5:1.

13. The orthodontic bracket of claim 12, further comprising a first tie-wing on said vertical member and a second tie-wing on said horizontal member to enable attachment of a fastening member to the bracket for securing the arch wire in said slot.

14. An orthodontic bracket for use with an arch wire to apply corrective forces to a tooth, comprising:
a substantially vertical element having a slot formed therein for receiving the arch wire; and
a substantially horizontal element connected to said vertical element with said vertical element being positioned gingivally with respect to said horizontal element, said horizontal element having opposing first and second ends extending away from said vertical element and defining a pair of spaced-apart wire engaging points engageable with the arch wire for enabling proper rotational control of the bracket during use, said horizontal member having at the ends thereof horizontally extending wings for engaging stretched elastomeric modules thereby enhancing rotational control, said bracket including means for inhibiting contact between the arch wire and the horizontal element when the arch wire is engaged with at least one of the wire engaging points to reduce friction between the arch wire and the horizontal element.

15. A method of using an orthodontic bracket with an arch wire for correcting the position of a tooth, the bracket having a substantially vertical element having a slot formed therein for receiving the arch wire, and a substantially horizontal element connected to the vertical element with the vertical element being positioned gingivally with respect to the horizontal element, the horizontal element having opposing first and second ends extending away from the vertical element and defining a pair of spaced-apart wire engaging points engageable with the arch wire for enabling proper rotational control of the bracket during use, the slot in the vertical element being vertically spaced apart from the horizontal element to limit contact between the arch wire and the horizontal element and wherein the ratio of the distance between the wire engaging points to the length of the slot is approximately 3.5:1, the method comprising the steps of:
applying the bracket to the tooth;
installing the arch wire within the slot in the bracket; and
attaching a force transmitting member to the bracket for applying a force to the bracket initially causing the crown of the tooth to tilt relative to a vertical axis through the tooth and thereby causing the arch wire to contact one of the wire engaging points and a part of the vertical element defining an upper portion of the slot that is distal to the one wire engaging point such that further force applied by the force transmitting member causes a reverse tilt of the root of the tooth relative to the vertical axis, thereby correcting the position of the tooth.

* * * * *